US011804283B2

(12) United States Patent
Shaver et al.

(10) Patent No.: US 11,804,283 B2
(45) Date of Patent: Oct. 31, 2023

(54) PREDICTING MOLECULAR PROPERTIES OF MOLECULAR VARIANTS USING RESIDUE-SPECIFIC MOLECULAR STRUCTURAL FEATURES

(71) Applicant: Just-Evotec Biologics, Inc., Seattle, WA (US)

(72) Inventors: Jeremy Martin Shaver, Lake Forest Park, WA (US); Randal Robert Ketchem, Snohomish, WA (US)

(73) Assignee: Just-Evotec Biologics, Inc., Seattle, WA (US)

( * ) Notice: Subject to any disclaimer, the term of this patent is extended or adjusted under 35 U.S.C. 154(b) by 732 days.

(21) Appl. No.: 16/620,389

(22) PCT Filed: Jun. 8, 2018

(86) PCT No.: PCT/US2018/036777
§ 371 (c)(1),
(2) Date: Dec. 6, 2019

(87) PCT Pub. No.: WO2018/227167
PCT Pub. Date: Dec. 13, 2018

(65) Prior Publication Data
US 2020/0143904 A1 May 7, 2020

Related U.S. Application Data

(60) Provisional application No. 62/517,048, filed on Jun. 8, 2017.

(51) Int. Cl.
*G16B 20/00* (2019.01)
*G16B 30/00* (2019.01)
*G16B 40/00* (2019.01)
*G16B 20/30* (2019.01)
*G06F 30/20* (2020.01)
*G16B 35/00* (2019.01)
*G06F 111/10* (2020.01)
*G16B 20/50* (2019.01)

(52) U.S. Cl.
CPC .............. *G16B 20/30* (2019.02); *G06F 30/20* (2020.01); *G16B 20/00* (2019.02); *G16B 30/00* (2019.02); *G16B 35/00* (2019.02); *G16B 40/00* (2019.02); *G06F 2111/10* (2020.01); *G16B 20/50* (2019.02)

(58) Field of Classification Search
None
See application file for complete search history.

(56) References Cited

U.S. PATENT DOCUMENTS

2005/0278124 A1 12/2005 Duffy et al.
2016/0147936 A1* 5/2016 Vendruscolo .......... G16B 40/00
702/19

FOREIGN PATENT DOCUMENTS

WO WO-2018227167 A1 12/2018

OTHER PUBLICATIONS

Bhasin et al (J. Biosci., 2007, 32:31-42).*
Sydow et al (PLoS ONE, 2014, 9:e100736, p. 1-13).*
Sydow et al (PLoS ONE, 2014, 9:e100736, p. 1-13) Supplemental Information.*
Lippow et al (Nature Biotechnology, 2007, 25:1171-1176).*
Lippow et al (Nature Biotechnology, 2007, Supplementary Methods and Figures, p. 1-16).*
"European Application Serial No. 18735116.8, Response filed Jul. 24, 2020 to Communication Pursuant to Rules 161(1) and 162 EPC dated Jan. 17, 2020", 9 pgs.
"International Application Serial No. PCT/US2018/036777, International Preliminary Report on Patentability dated Dec. 19, 2019", 15 pgs.
"Japanese Application Serial No. 2019-568247, Notification of Reasons for Refusal dated May 17, 2022", w/ English translation, 7 pgs.
Pejaver, Vikas, et al., "Missense variant pathogenicity predictors generalize well across a range of function-specific prediction challenges", (Mar. 26, 2017), 1092-1108.
"International Application Serial No. PCT/US2018/036777, International Search Report dated Sep. 18, 2018", 5 pgs.
"International Application Serial No. PCT/US2018/036777, Written Opinion dated Sep. 18, 2018", 13 pgs.
Gerard, JP Van Westen, et al., "Benchmarking of protein descriptor sets in proteochemometric modeling (part 1): comparative study ot 13 amino acid descriptor sets", Journal of Cheminformatics. Biomed Central Ltd. London. UK. vol 5. No. 1., (Sep. 23, 2013), 41 pgs.
Hao, Lin, et al., "AcalPred: A Sequence-Based Tool for Discriminating between Acidic and Alkaline Enzymes", PLOS One, vol. 8. No. 10, (Oct. 9, 2013), e75726.
Lin, H, et al., "Prediction of thermophilic proteins using feature selection technique", Journal of Microbiological Methods, Elsevier. Amsterdam. NL, vol. 84. No. 1, (Oct. 31, 2010), 67-70.
Montanucci, L, "Predicting protein thermostability changes from sequence upon multiple mutations", Bioinformatics, vol. 24 No. 13, (Jun. 27, 2008), i190-i195.
Olga, Obrezanova, et al., "Aggregation risk prediction for antibodies and its application to biotherapeutic development", MABS, vol. 7. No. 2, (Mar. 4, 2015), 352-363.
Yang, Yang, et al., "PON-Sol: prediction of effects of amino acid substitutions on protein solubility", Bioinformatics, vol. 32. No. 13., (Feb. 19, 2016), 2032-2034.

(Continued)

*Primary Examiner* — Laura B Goddard
(74) *Attorney, Agent, or Firm* — Schwegman Lundberg & Woessner, P.A.

(57) ABSTRACT

A system for generating a model for predicting a molecular property of a variant of a molecule is provided. For each of a plurality of variants of the molecule, the system for each structural feature, aggregates the values for the structural features of the residues of the molecule that were modified to form the variant to form a feature vector for the variant. The system assigns the value for the molecular property of the variant to the feature vector wherein the feature vector and the assigned value form training data. The system then generates the model for predicting a value for the molecular property using the training data for the plurality of variants.

20 Claims, 7 Drawing Sheets

(56) References Cited

OTHER PUBLICATIONS

"European Application Serial No. 18735116.8, Communication Pursuant to Article 94(3) EPC dated Jan. 18, 2023", 10 pgs.
"European Application Serial No. 18735116.8, Response filed May 18, 2023 to Communication Pursuant to Article 94(3) EPC dated Jan. 18, 2023", 10 pages.

* cited by examiner

PREDICTING MOLECULAR PROPERTIES OF MOLECULAR VARIANTS USING RESIDUE-SPECIFIC MOLECULAR STRUCTURAL FEATURES

CROSS-REFERENCE TO RELATED APPLICATIONS

This application is a U.S. national stage filing under 35 U.S.C. 371 from International Application No. PCT/US2018/036777, filed on 8 Jun. 2018, and published as WO 2018/227167 on 13 Dec. 2018, which claims the benefit of priority to U.S. Provisional Application Ser. No. 62/517,048, filed Jun. 8, 2017, which applications are incorporated herein by reference in their entirety.

BACKGROUND

Because the cost of developing breakthrough therapeutics based on modern biotechnology is so high, such therapeutics are not available to most people. A contributing factor to the high cost is that it is difficult to identify the molecular properties of new variants of a molecule such as an antibody. Although various tools are available to help in determining the molecular properties of molecules, they rely in large part in being able to synthesize the variant, which itself can be costly and time consuming.

DETAILED DESCRIPTION

Figure 1:
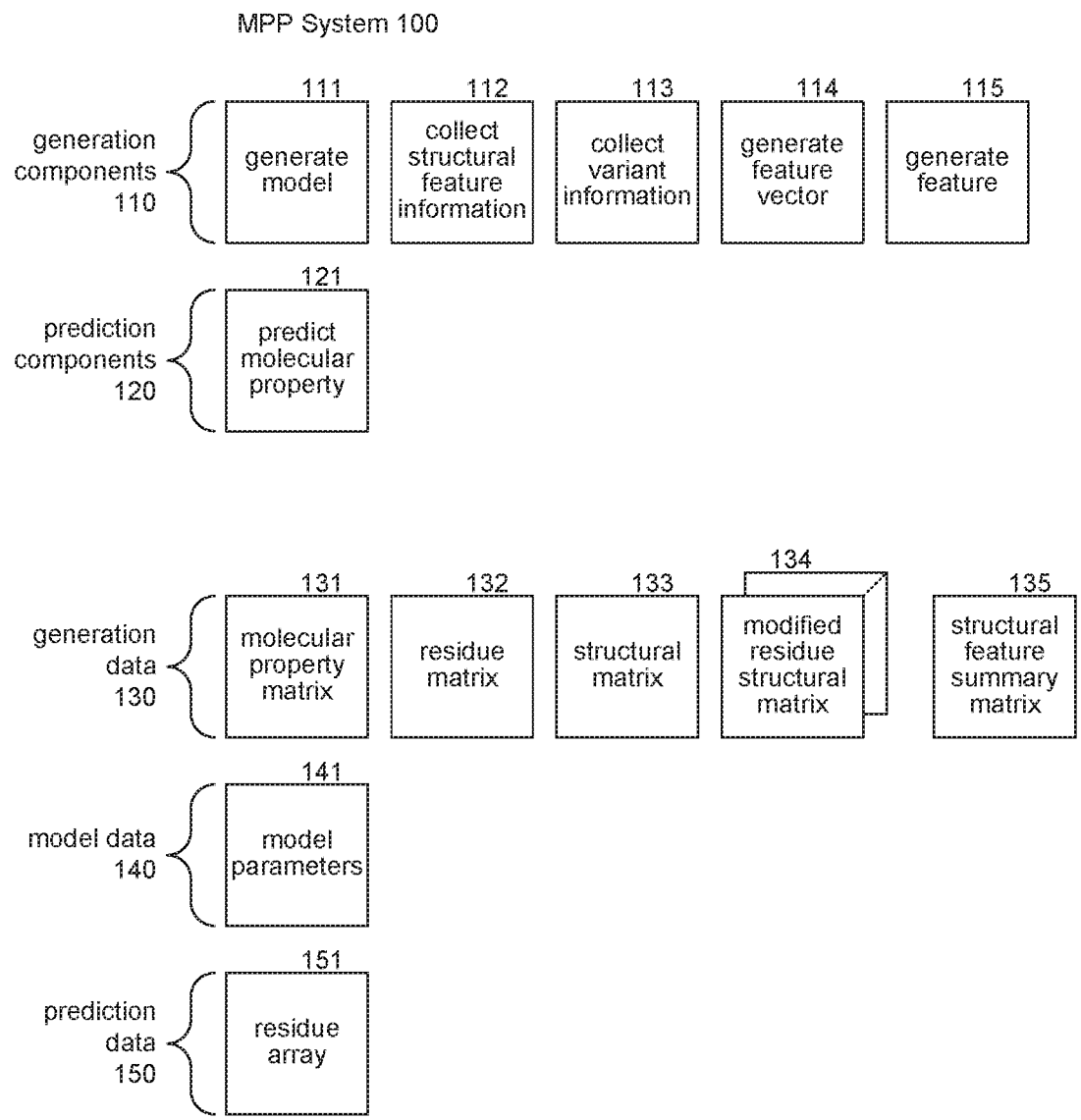
FIG. 1 is a block diagram illustrating components of the MPP system in some embodiments.

A method and system for estimating molecular properties of new variants of a parent molecule (e.g., an antibody molecule) prior to synthesis of the new variants is provided. In some embodiments, a molecular property prediction ("MPP") system uses of various structural features of residues in a parent molecule (referred to as a molecule) in conjunction with molecular properties measured for a set of variants of the molecule. The MPP system supports predicting molecular properties of a new variant without having to calculate structural models for each of the variants. The MPP system also avoids creating the much more complicated "all molecules" model which attempts to predict molecular properties for any general antibody. The MPP system provides a prediction model that is more specific to a given molecule and more robust than the "all molecules" model. In some embodiments, the MPP system predicts molecular properties that include, but are not limited to, molecular characterizations such as antibody melting temperature ("Tm"), the percentage of high molecular weight expected during the expression and purification of the variant ("HMW"), chemical unfolding behavior, solubility, viscosity, and aggregation behavior (e.g., self-interaction nanoparticle spectroscopy—"SINS").

In some embodiments, the MPP system generates a model for predicting a molecular property of a variant of a molecule. The MPP system accesses values for structural features of the residues of the molecule. For example, the structural features of a molecule may include participation of the residue in charge patches or hydrophobic patches and group diversity of neighboring residues. For each variant of the molecule, the MPP system accesses variant information indicating which residues in a sequence of residues of the molecule were modified to form the variant and a value for the molecular property of the variant. For each structural feature, the MPP system aggregates the values for the structural features of the residues of the molecule that were modified to form the variant to generate a feature vector for the variant. The MPP system assigns the value for the molecular property of the variant to the feature vector. The feature vector and the assigned value for each variant form training data. The MPP system then uses the training data to generate the prediction model for predicting a value for the molecular property. For example, the MPP system may use a linear regression technique, neural networks, random forest techniques, Lasso regression techniques, and partial least square regression techniques to generate the prediction model. The MPP system may generate a separate prediction model for each molecular property.

After the prediction model is generated, the MPP system can then use the prediction model to predict values for a molecular property for a new variant of the molecule without having to synthesize the new variant and provide information to help guide future variant creation and experimentations. The MPP system inputs an indication of the residues of the molecule that are to be changed (e.g., by substituting one amino acid for another). The MPP system generates a new feature vector for the variant in a manner similar to how the feature vectors of the training data are generated. The MPP system then applies the prediction model for a molecular property to the new feature vector to predict the value for the molecular property.

FIG. 1 is a block diagram illustrating components of the MPP system in some embodiments. The MPP system 100 includes generation components 110 prediction components 120, generation data 130, model data 140, and prediction data 150. The generation components include a generate model component 111, a collect structural feature information component 112, a collect variant information component 113, a generate feature vector component 114, and a generate feature component 115. The generate model component 111 controls the overall generation of the model by invoking the collect structural feature information component 112, the collect variant information component 113, and the generate feature vector component 114 and then training the model. The collect structural feature information component 112 collects the values for the structural features for the residues of the molecule. The structural features information is stored in a structural matrix 133 that includes a row for each residue and a column for each feature with entries indicating the values of a feature for a residue of the molecule. The collect variant information component 113 collects information on the variants of the molecules that includes which residues of the molecule were modified and a value for each molecular property for the variant. The information relating to the modified variants is stored in a residue matrix 132 that includes a row for each variant and a column for each residue with the entries indicating whether that residue is modified in that variant. The information related to the values for the molecular property are stored in a molecular property matrix 131 that includes a row for each variant and a column for each molecular property with the entries indicating the values for each molecular property for each variant. The generate feature vector component 114 generates a feature vector of features for each variant. The feature vector for a variant includes, for each structural feature, one or more statistics generated from the values for that structural feature of the residues of that variant that were modified. To generate a feature vector for a variant, the generate feature vector component 114 may generate a modified residue structural matrix 134 for that variant that includes a column for each modified residue of that variant and a row for each feature with entries indicating the values for that structural feature in that residue for the molecule. The generate feature component 115 then aggregates the values from the modified residue structural matrix 134 for a variant. The generate feature component 115 may generate a structural feature summary matrix 135 that includes a row for each variant and a column for each feature with entries indicating the value for the feature that may be a statistic such as sum, mean, and standard deviation for that variant. Each row of the structural feature summary matrix 135 represents the feature vector for a variant. The generate model component then assigns to each feature vector of a variant the value of its molecular property from the molecular property matrix 131.

The generate model component 111 then trains the prediction model using the feature vectors with their assigned values. The generate model component 111 stores the parameters learned during the training in a model parameters store 141. Once the prediction model is generated, the value of a molecular property for a new variant can be predicted using a predict molecular property component 121. The predict molecular property component inputs a residue array 151 that indicates for each residue of the molecule whether the corresponding residue in the new variant has been modified. The predict molecular property component 121 invokes the generate feature vector component to generate a new feature vector for the new variant. The predict molecular property component 121 then applies the model to the new feature vector to predict the value for the molecular property of the new variant.

The matrices below provide example values for the various matrices of the MPP system. The structural matrix is generated for variant 2. The modified residue structural matrix includes the three rows of the structural matrix corresponding to the entries of the residue matrix that have values of "true." The structural feature summary matrix includes a row for each variant with a column for each statistic—the maximum, mean, and standard deviation for each of the hydrophobic area, the positive area, and solvent accessibility ("SA") structural features. For example, the maximum, mean, and standard deviation ("SD") of the positive area for variant 2 are 180, 60, and 84.853, respectively.

Molecular Property Matrix

| | Molecular Property |
|---|---|
| Variant | HMW |
| 1 | 0.60083 |
| 2 | 0.87401 |
| 3 | 0.53155 |

Residue Matrix

| | Residue | | | | |
|---|---|---|---|---|---|
| Variant | 1 | 2 | 3 | 4 | 5 |
| 1 | False | False | False | True | True |
| 2 | True | False | False | True | True |
| 3 | False | True | True | True | True |

Structural Matrix

| | Structural Feature | | |
|---|---|---|---|
| Residue | hydrophobic area | positive area | SA |
| 1 | 0 | 0 | 36.1 |
| 2 | 0 | 0 | 23.5 |
| 3 | 110 | 180 | 57.1 |
| 4 | 0 | 180 | 199.1 |
| 5 | 0 | 0 | 84.7 |

Modified Residue Structural Matrix (for Variant 2)

| | Structural Feature | | |
|---|---|---|---|
| Residue | hydrophobic area | positive area | SA |
| 1 | 0 | 0 | 36.1 |
| 4 | 0 | 180 | 199.1 |
| 5 | 0 | 0 | 84.7 |

Structural Feature Summary Matrix

| | Statistic | | | | | | | | |
|---|---|---|---|---|---|---|---|---|---|
| | SA | | | hydrophobic area | | | positive area | | |
| Variant | max | mean | SD | max | mean | SD | max | mean | SD |
| 1 | 199.1 | 141.9 | 57.2 | 0 | 0 | 0 | 180 | 90 | 90 |
| 2 | 199.1 | 106.63 | 68.328 | 0 | 0 | 0 | 180 | 60 | 84.853 |
| 3 | 199.1 | 91.1 | 66.014 | 110 | 27.5 | 47.631 | 180 | 90 | 90 |

The computing systems on which the MPP system may be implemented may include a central processing unit, input devices, output devices (e.g., display devices and speakers), storage devices (e.g., memory and disk drives), network interfaces, graphics processing units, and so on. The input devices may include keyboards, pointing devices, touch screens, gesture recognition devices (e.g., for air gestures), head and eye tracking devices, microphones for voice recognition, and so on. The computing systems may include desktop computers, laptops, tablets, servers, and so on. The computing systems may access computer-readable media that include computer-readable storage media and data transmission media. The computer-readable storage media are tangible storage means that do not include a transitory, propagating signal. Examples of computer-readable storage media include memory such as primary memory, cache memory, and secondary memory (e.g., DVD) and other storage. The computer-readable storage media may have recorded on it or may be encoded with computer-executable instructions or logic that implements the MPP system. The data transmission media is used for transmitting data via transitory, propagating signals or carrier waves (e.g., electromagnetism) via a wired or wireless connection.

The MPP system may be described in the general context of computer-executable instructions, such as program modules and components, executed by one or more computers, processors, or other devices. Generally, program modules or components include routines, programs, objects, data structures, and so on that perform particular tasks or implement particular data types. Typically, the functionality of the program modules may be combined or distributed as desired in various examples. Aspects of the MPP system may be implemented in hardware using, for example, an application-specific integrated circuit (ASIC) or field programmable gate array ("FPGA").

In some embodiments, the actual molecular properties are measured for each previously synthesized variant (i.e., that are used for training) and are referred to as the "Y values." A separate value is collected for each variant (rows) and each molecular property (e.g. Tm, HMW, SINS—as columns) in the molecular property matrix 131.

In some embodiments, the residue matrix 132 is a Boolean matrix that describes which residue(s) were modified in the parent molecule to create the given variant. Each row of this matrix represents one variant and each column a Boolean vector indicating if a given residue was mutated.

In some embodiments, the structural features of the molecule for each residue that is available for modification in the molecule is stored in the structural matrix 133. The structural matrix 133 contains columns representing the individual structural features and rows as the residues. The structural matrix 133 may be derived from a structural model of the molecule by extracting for each residue, value for structural features such as:

- participation of the residue in positive or negative charge patches or hydrophobic patches
- group diversity of neighboring residues (e.g. number of hydrophobic, acidic, basic, or neutral residues within a given distance—distance based on the tertiary structure)
- solvent accessibility of the residue (high at the surface of the molecule)
- nearness to region/chain interfaces (e.g. distance to Fv and constant domain interface)
- secondary structure environment
- original (in molecule) and new residue (in variant) length or size
- original and new residue pKa (i.e., acidity)

A goal of the MPP system may be to identify a subset of structural features that can be used to estimate a given molecular property for both the set of previously synthesized variants (known as a calibration set) and to estimate the molecular property for new variants (without the synthesis and measurement of the molecular property of those variants). The MPP system starts by using the residue matrix 132 to extract the rows of the structural matrix 133 for residues that were modified for a given variant. The modified residue structural matrix 134 for a variant has as many rows as the number of residues modified for that variant. The modified residue structural matrix 134 is compressed down into a single row by applying a set of statistical metrics to each column including, but not necessarily limited to: sum, mean, standard deviation, skew, kurtosis, minimum, maximum, product, and sum and mean of the log of absolute values (e.g., logs post-multiplied by original value sign either summed or averaged). The result of applying each of these operations on each original structural feature column is that the statistic is turned into a new column. Accordingly, there are 10 new columns (e.g., given the set of 10 statistical metrics above) for each original structural feature. The MPP system thus captures the molecular variation of the set of modified residues without having to specifically list the residues. After iterating over all variants, the MPP system generates a structural feature summary matrix 135 in which each row is a variant and the columns are the statistical summary of each set of modified structural features. Next, the structural feature summary matrix 135 is either used in a dimension-reducing regression or classification model (e.g., partial least squares, or neural network with reducing hidden-layer nodes) to predict the Y values (e.g., molecular properties), or it is used in a variable selection method (e.g., a genetic algorithm, or correlation-based selection) to reduce the number of variables. In the latter case, only the selected variables are used in a regression or classification model.

In some embodiments, the MPP system may support molecule-generalized models. Because each molecule has a different starting value for a given molecular property, and because each molecule may be differently sensitive to the characteristics of the modified residues, models as described above are expected to only be applicable to the specific parent molecule. However, some property predictions can be made less molecule-specific by adding molecule-encoding variables or doing a priori corrections, for example, by making the Y values be relative to the parent molecule. In such cases, multiple structural feature summary matrices for different molecules may be combined along with their corresponding Y values and processed in a single model. For example, a combined structural feature summary matrix may include a column to identify the parent molecule of a variant. In such a case, the MPP system may use deep-learning style models such a neural network with multiple hidden layers.

Figure 2:
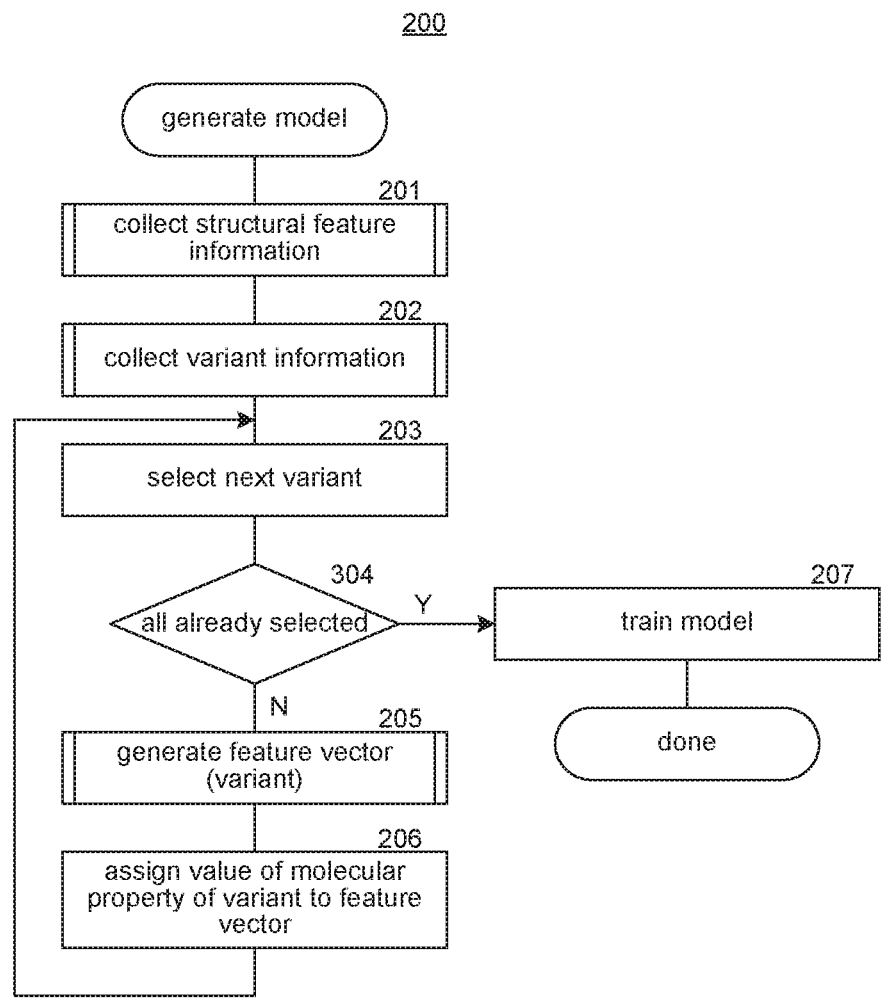
FIG. 2 is a flow diagram that illustrates the processing of a generate model component of the MPP system in some embodiments.

FIG. 2 is a flow diagram that illustrates the processing of a generate model component of the MPP system in some embodiments. The generate model component 200 is invoked to generate the model for a molecule for use in predictions. In block 201, the component invokes the collect structural feature information component to collect the structural features of the molecule. In block 202, the component invokes the collect variant information component to collect variant information for each variant that is used to generate the model. In blocks 203-206, the component loops generating the feature vector for each variant. In block 203, the component selects the next variant. In decision block 204, if all variants have already selected, then the component continues at block 207, else the component continues at block 205. In block 205, the component invokes the generate feature vector component passing an indication of the variant. In block 206, the component assigns the value of the molecular property for the variant to the feature vector to form the training data of the feature vector and the assigned value. The component then loops to block 203 to select the next variant. In block 207, the component trains the prediction model using the training data and completes.

Figure 3:
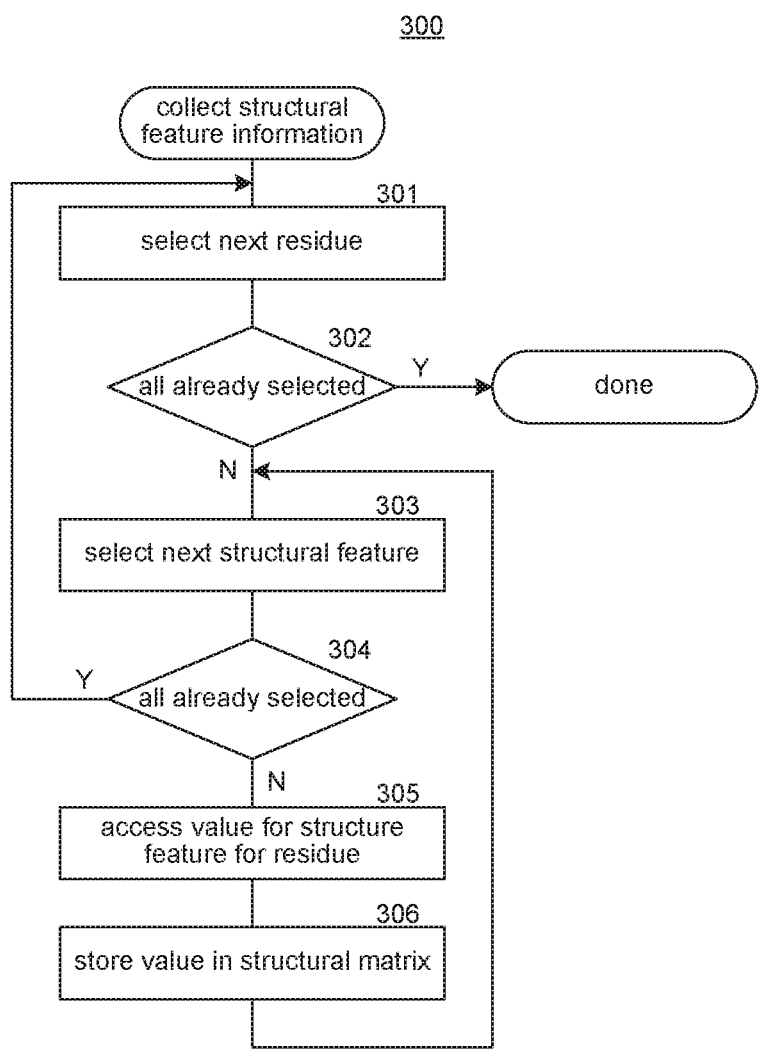
FIG. 3 is a flow diagram that illustrates the processing of a collect structural feature information component of the MPP system in some embodiments.

FIG. 3 is a flow diagram that illustrates the processing of a collect structural feature information component of the MPP system in some embodiments. The collect structural feature information component 300 is invoked to collect the structural features for the molecule. In block 301, the component selects the next residue of the molecule. In decision block 302, if all the residues have already been selected, then the component completes, else the component continues at block 303. In block 303, the component selects the next structural feature of the residue. In decision block 304, if all the structural features for the selected residue have already been selected, then the component loops to block 301 to select the next residue, else the component continues at block 305. In block 305, the component accesses the value for the structural feature for the selected residue. In block 306, the component stores the value in the structural matrix 133 and then loops to block 303 to select the next structural feature.

Figure 4:
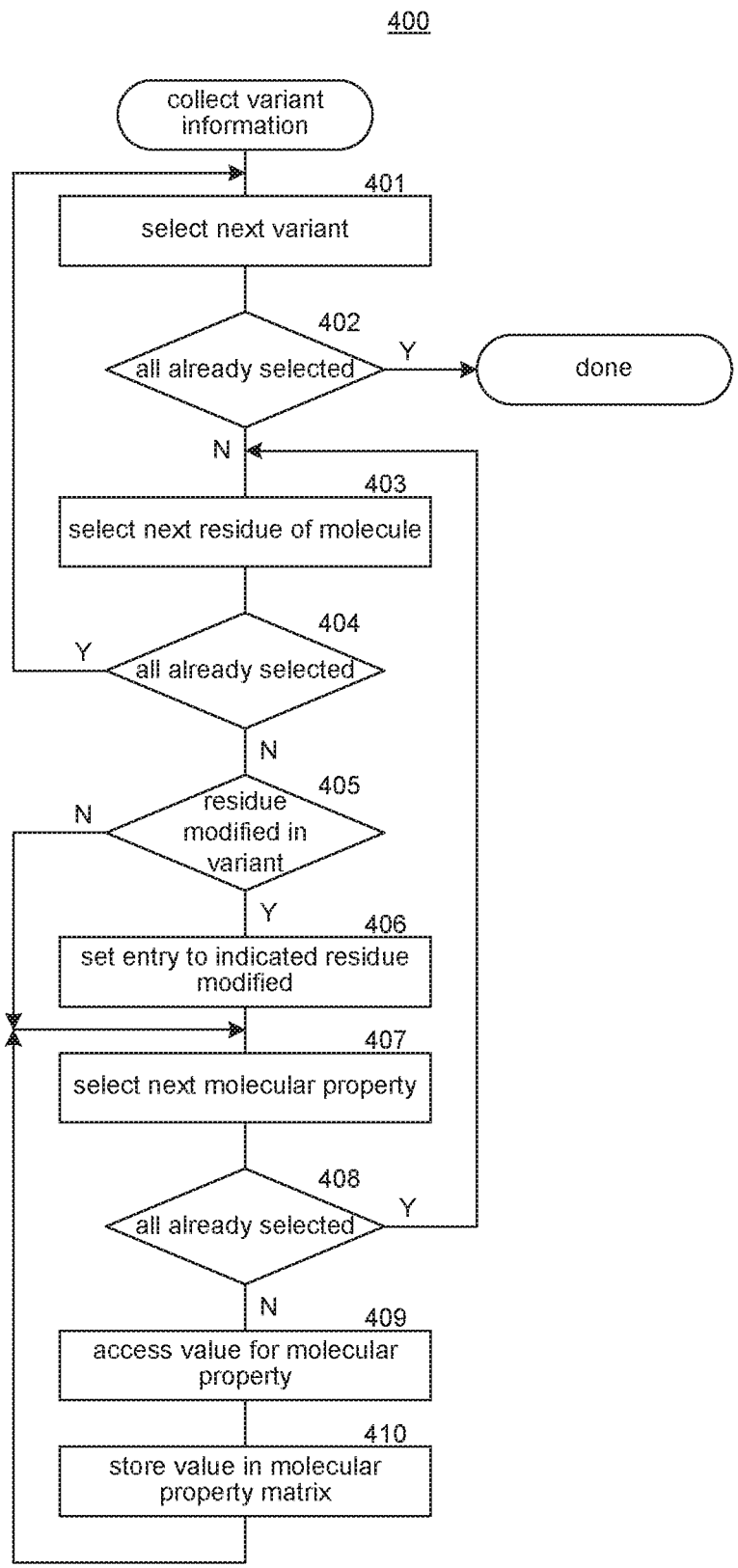
FIG. 4 is a flow diagram that illustrates the processing of a collect variant information component of the MPP system in some embodiments.

FIG. 4 is a flow diagram that illustrates the processing of a collect variant information component of the MPP system in some embodiments. The collect variant information component 400 is invoked to collect the molecular properties of the variants along with an indication of which residues were modified. In block 401, the component selects the next variant. In decision block 402, if all the variants have already been selected, then the component completes, else the component continues at block 403. In block 403, the component selects the next residue of the molecule. In decision block 404, if all the residues have already been selected, then the component loops to block 401 to select the next variant, else the component continues at block 405. In decision block 405, if the residue is modified in the variant, then the component continues at block 406, else the component continues at block 407. In block 406, the component sets the entry for the selected variant and the selected residue in the residue matrix 132 to indicate that the residue has been modified in the selected variant. In block 407, the component selects the next molecular property. In decision block 408, if all the molecular properties have already been selected, then the component loops to block 403 to select the next residue in the molecule, else the component continues at block 409. In block 409, the component accesses the value for the molecular property. In block 410, the component stores the value in the molecular property matrix 131 and then loops to block 407 to select the next molecular property.

Figure 5:
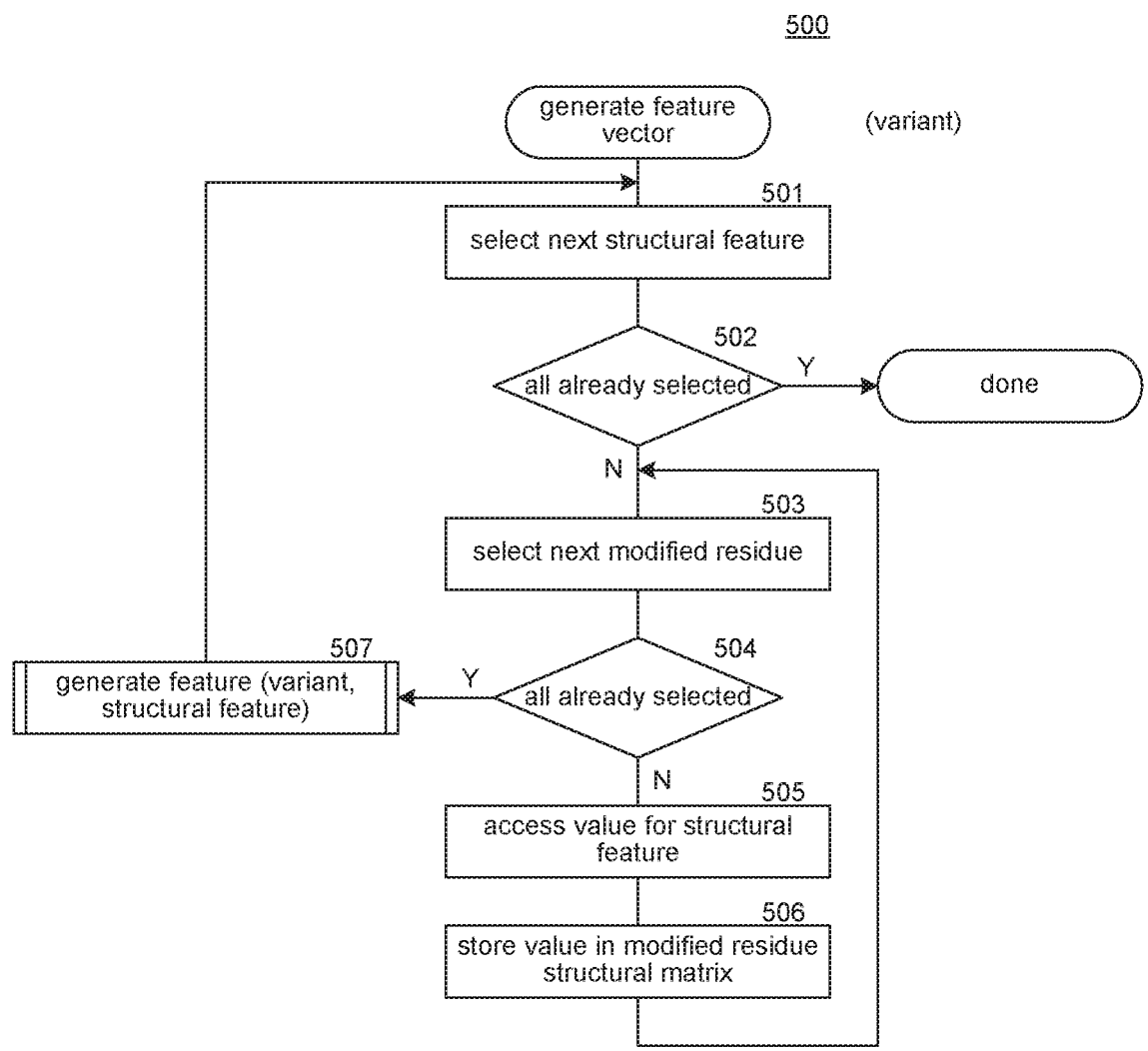
FIG. 5 is a flow diagram that illustrates the processing of a generate feature vector component of the MPP system in some embodiments.

FIG. 5 is a flow diagram that illustrates the processing of a generate feature vector component of the MPP system in some embodiments. A generate feature vector component 500 is invoked to generate a feature vector for a passed variant. In block 501, the component selects the next structural feature. In decision block 502, if all the structural features have already been selected, then the component completes, else the component continues at block 503. In block 503, the component selects the next modified residue for the passed variant. In decision block 504, if all the modified residues have already been selected, then the component continues at block 507, else the component continues at block 505. In block 505, the component accesses the value for the selected structural feature. In block 506, the component stores the value in the modified residue structural matrix 134 for the variant and then loops to block 503 to select the next modified residue. In block 507, the component invokes a generate feature component to generate the features for the variant from the value for the selected structural feature stored in the modified residue structural matrix 134 and then loops to block 501 to select the next structural feature.

Figure 6:
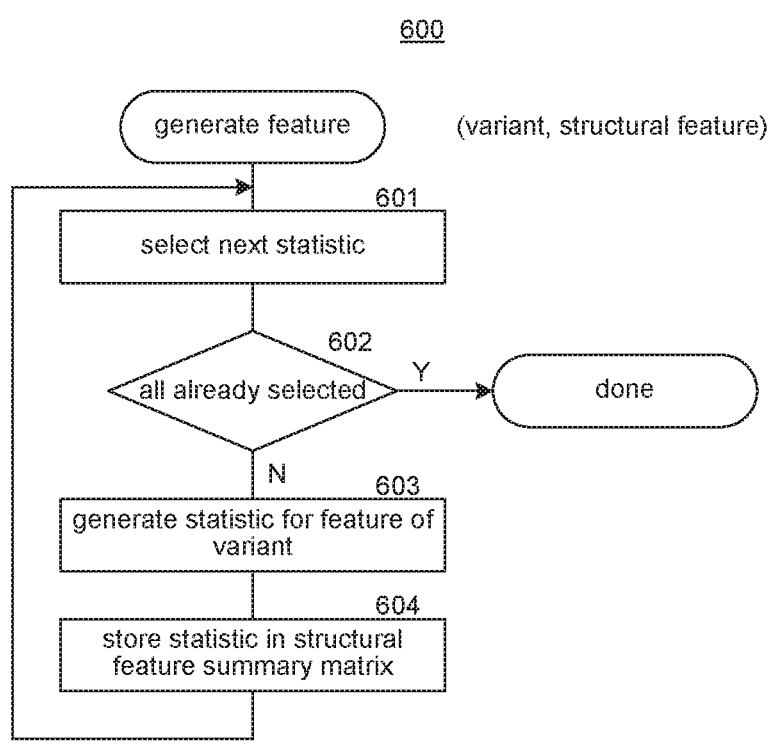
FIG. 6 is a flow diagram that illustrates the processing of a generate feature component of the MPP system in some embodiments.

FIG. 6 is a flow diagram that illustrates the processing of a generate feature component of the MPP system in some embodiments. The generate feature component 600 is passed an indication of a variant and a structural feature and generates a feature for the feature vector for the variant for each statistic based on the structural feature. In block 601, the component selects the next statistic. In decision block 602, if all the statistics have already been selected, then the component completes, else the component continues at block 603. In block 603, the component generates the selected statistic for the structural feature of the variant based on values in the modified residue structural matrix 134 for the passed variant. In block 604, the component stores the statistic in the structural feature summary matrix 135 and then loops to block 601 to select the next statistic.

Figure 7:
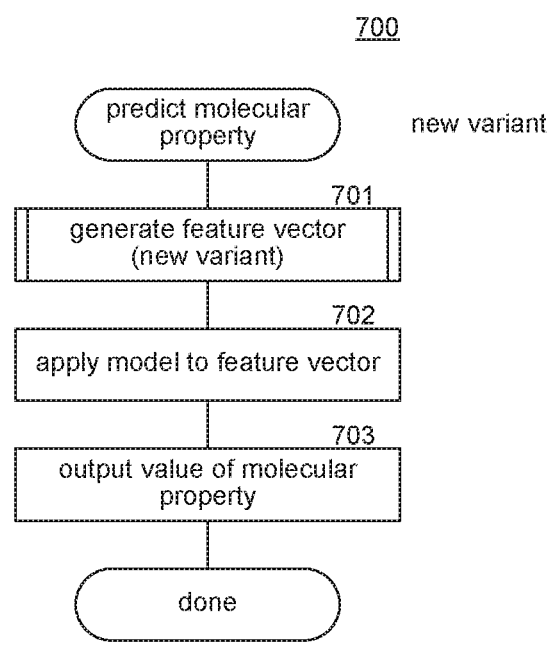
FIG. 7 is a flow diagram that illustrates the processing of a predict molecular property component of the MPP system in some embodiments.

FIG. 7 is a flow diagram that illustrates the processing of a predict molecular property component of the MPP system in some embodiments. The predict property component 700 is invoked to predict a molecular property of a new variant. The new variant is indicated by the residues that have been modified. In block 701, the component invokes a generate feature vector component to generate a feature vector for the new variant based on the modified residues as indicated by the residue array 151. In block 702, the component applies the prediction model to the feature vector to generate a value for a molecular property for the new variant. In block 703, the component outputs of value of the molecular property and then completes.

The following paragraphs describe various embodiments of aspects of the MPP system. An implementation of the MPP system may employ any combination of the embodiments. The processing described below may be performed by a computing device with a processor that executes computer-executable instructions stored on a computer-readable storage medium that implements the MPP system.

In some embodiments, a method performed by a computing system for generating a model for predicting a molecular property of a variant of a molecule is provided. The method accesses values for structural features of residues of the molecule. For each of a plurality of variants of the molecule, the method accesses variant information indicating which residues in a sequence of residues of the molecule were modified to form the variant and a value for the molecular property of the variant. For each of the plurality of variants of the molecule, the method also, for each structural feature, aggregates the values for the structural features of the residues of the molecule that were modified to form the variant to form a feature vector for the variant. For each of the plurality of variants of the molecule, the method assigns the value for the molecular property of the variant to the feature vector wherein the feature vector and the assigned value form training data. The method then generates the model for predicting a value for the molecular property using the training data for the plurality of variants. In some embodiments, the method further predicts a value for the molecular property of a new variant by accessing new variant information indicating which residues in the sequence of residues of the molecule were modified to form the variant; for each structural feature, aggregates the values for the structural feature of the residues of the molecule that were modified to form the new variant to form a new feature vector for the new variant; and applies the model to the new feature vector to predict the value for the molecular property of the new variant. In some embodiments, the model is generated using a linear regression technique using the training data as input. In some embodiments, the model is generated by learning a neural network using the training data as input. In some embodiments, the generating of the model includes reducing dimensions of the training data. In some embodiments, the molecule is a protein. In some embodiments, a variant is formed by replacing an amino acid of the molecule with a different amino acid. In some embodiments, the molecular property is selected from a group consisting of antibody melting temperature, percentage of high molecular weight, chemical unfolding behavior, solubility, viscosity, and aggregation behavior. In some embodiments, the structural features are selected from a group consisting of participating of a residue in charge patches or hydrophobic patches, group diversity of neighboring residues, solvent accessibility of a residue, nearness to region/chain interfaces, secondary structural environment, sizes of residue in the molecule and the variant, and acidity of a residue in the molecule and the variant. In some embodiments, the aggregating of the values for a structural feature generates statistics selected from a group consisting of sum, mean, standard deviation, skew, kurtosis, minimum, maximum, product, sum of log of absolute values, and mean of log of absolute values.

In some embodiments, a computing system for predicting a value for a molecular property of a new variant of a molecule is provided. The computing system includes one or more computer-readable storage medium storing computer-executable instructions and one or more processors for executing the computer-executable instructions stored in the one or more computer-readable mediums. The computer-executable instructions control the computing system to access new variant information indicating which residues in a sequence of residues of the molecule were modified to form the new variant. For each of a plurality of structural features of residues of the molecule, the computer-executable instructions control the computing system to aggregate the values for the structural feature of the residues of the molecule that were modified to form the new variant to form a new feature vector for the new variant. The computer-executable instructions further control the computing system apply a model to the new feature vector to predict the value for the molecular property of the new variant. The model is generated using training data comprising feature vectors derived from value of structural features of variants of the molecule and the values of the molecular property of those variants. In some embodiments, the computer-executable instructions further control the computing system to access values for structural features of residues of the molecule. For each of a plurality of variants of the molecule, the computer-executable instructions control the computing system to access variant information indicating which residues in a sequence of residues of the molecule were modified to form the variant and a value for the molecular property of the variant; for each structural feature, aggregate the values for the structural features of the residues of the molecule that were modified to form the variant to form the feature vector for the variant; and assign the value for the molecular property of the variant to the feature vector wherein the feature vector and the assigned value form the training data. The computer-executable instructions control the computing system to generate the model for predicting a value for the molecular property using the training data for the plurality of variants. In some embodiments, the model is generated using a linear regression technique using the training data as input. In some embodiments, the model is generated by learning a neural network using the training data as input. In some embodiments, the computer-executable instructions further control the computing system to reduce dimensions of the training data. In some embodiments, the molecule is a protein. In some embodiments, a variant is formed by replacing an amino acid of the molecule with a different amino acid. In some embodiments, the molecular property is selected from a group consisting of antibody melting temperature, percentage of high molecular weight, chemical unfolding behavior, solubility, viscosity, and aggregation behavior. In some embodiments, the structural features are selected from a group consisting of participating of a residue in charge patches or hydrophobic patches, group diversity of neighboring residues, solvent accessibility of a residue, nearness to region/chain interfaces, secondary structural environment, sizes of residue in the molecule and the variant, and acidity of a residue in the molecule and the variant. In some embodiments, the computer-executable instructions control the computing system to aggregate the values for a structural feature further generate statistics selected from a group consisting of sum, mean, standard deviation, skew, kurtosis, minimum, maximum, product, sum of log of absolute values, and mean of log of absolute values.

Although the subject matter has been described in language specific to structural features and/or acts, it is to be understood that the subject matter defined in the appended claims is not necessarily limited to the specific features or acts described above. Rather, the specific features and acts described above are disclosed as example forms of implementing the claims. Accordingly, the invention is not limited except as by the appended claims.

We claim:

1. A method comprising:
performing, by a computing system including one or more processing units and one or more non-transitory computer-readable storage media, a training process for a model to predict values for a molecular property for new variant proteins that correspond to a parent protein, the training process including:
determining, by the computing system, a plurality of sequences of variant proteins of the parent protein, individual variant proteins of the plurality of variant proteins having at least one modified residue at a position of a sequence of the individual variant protein that is different from an initial residue at a corresponding position of a sequence of the parent protein;
determining, by the computing system, first values for a plurality of structural features with respect to modified residues of the plurality of variant proteins;
generating, by the computing system, a plurality of structural matrices for the plurality of variant proteins, individual structural matrices of the plurality of structural matrices corresponding to a variant protein of the plurality of variant proteins and indicating a portion of the first values for the plurality of structural features for one or more modified residues of the variant protein;
for individual structural matrices of the plurality of structural matrices, performing, by the computing system, one or more statistical operations with respect to the portion of the first values for the plurality of structural features of the individual variant protein that corresponds to the individual structural matrix to produce one or more second values with individual second values of the one or more second values corresponding to an individual statistical operation of the one or more statistical operations;

for individual variant proteins of the plurality of variant proteins, generating, by the computing system, a structural feature summary matrix that includes the one or more second values associated with the individual variant protein, such that a plurality of structural feature summary matrices are produced with respect to the plurality of variant proteins;

determining, by the computing system and based on the plurality of structural feature summary matrices, a subset of the plurality of structural features;

for the individual variant proteins of the plurality of variant proteins, assigning, by the computing system, a value of the molecular property for the individual variant protein to the modified structural matrix associated with the individual variant protein;

producing, by the computing system, training data that includes the plurality of structural feature summary matrices and a plurality of values of the molecular property for the plurality of variant proteins, individual values of the plurality of values of the molecular property corresponding to an individual structural feature summary matrix of the plurality of structural feature summary matrices and an individual variant protein of the plurality of variant proteins; and generating, by the computing system and based on the training data, a model to predict additional values for the molecular property for new variant proteins that correspond to the parent protein, the model including one or more parameters that correspond to the subset of the plurality of structural features;

accessing, by the computing system, new variant information indicating one or more additional modified residues of a new variant protein that are different from one or more residues of the parent protein at one or more corresponding positions;

generating, by the computing system, an additional structural feature summary matrix for the new variant protein that indicates additional values for the subset of the plurality of structural features for the one or more modified residues; and applying, by the computing system, the model to the additional structural feature summary matrix to determine an additional value of the molecular property for the new variant protein.

2. The method of claim 1, comprising:
determining respective first values of the plurality of structural features for the modified residues of the plurality of variant proteins using structural models of the plurality of variant proteins.

3. The method of claim 1, wherein the parent protein and the plurality of variant proteins include antibodies and determining a value of an individual structural feature of the plurality of structural features for a modified residue of a variant protein of the plurality of variant proteins includes determining a distance between the modified residue and a constant region of the variant protein or determining a distance between the modified residue and a variable region of the variant protein.

4. The method of claim 1, comprising:
synthesizing a variant protein of the plurality of variant proteins; and
measuring the value of the molecular property for the variant protein.

5. The method of claim 1, wherein the one or more additional modified residues are indicated by an array that indicates, for each residue of the new variant protein, whether a respective residue in the new variant protein has been changed with respect to a residue at a corresponding location in the parent protein.

6. A computing system comprising:
one or more processing units; and
one or more non-transitory computer-readable storage media storing computer-executable instructions that, when executed by the one or more processing units, cause the computing system to:

perform a training process for a model to predict values for a molecular property for new variant proteins that correspond to a parent protein, the training process including:
  determining a plurality of sequences of variant proteins of the parent protein, individual variant proteins of the plurality of variant proteins having at least one modified residue at a position of a sequence of the individual variant protein that is different from an initial residue at a corresponding position of a sequence of the parent protein;
  determining first values for a plurality of structural features with respect to modified residues of the plurality of variant proteins;
  generating a plurality of structural matrices for the plurality of variant proteins individual structural matrices of the plurality of structural matrices indicating a portion of the first values for the plurality of structural features for one or more modified residues of the variant protein;
  for individual structural matrices of the plurality of structural matrices, performing, by the computing system, one or more statistical operations with respect to the portion of the first values for the plurality of structural features of the individual variant protein that corresponds to the individual structural matrix to produce one or more second values with individual second values of the one or more second values corresponding to an individual statistical operation of the one or more statistical operations;
  for individual variant proteins of the plurality of variant proteins, generating a structural feature summary matrix that includes the one or more second values associated with the individual variant protein, such that a plurality of structural feature summary matrices are produced with respect to the plurality of variant proteins;
  determining, based on the plurality of structural feature summary matrices, a subset of the plurality of structural features;
  for individual variant proteins of the plurality of variant proteins, assigning a value of a molecular property for the individual variant proteins to the modified structural matrix associated with the individual variant protein;

producing training data that includes the plurality of structural feature summary matrices and a plurality of values of the molecular property for the plurality of variant proteins, individual values of the plurality of values of the molecular property corresponding to an individual structural feature summary matrix of the plurality of structural feature summary matrices and an individual variant protein of the plurality of variant proteins; and generating, based on the training data, a model to predict additional values for the molecular property for new variant proteins that correspond to the parent protein, the model including one or more parameters that correspond to the subset of the plurality of structural features;

access new variant information indicating one or more additional modified residues of a new variant protein that are different from one or more residues of the parent protein at one or more corresponding positions;

generate an additional structural feature summary matrix for the new variant protein that indicates additional values for the subset of the plurality of structural features for the one or more modified residues; and apply the model to the additional structural feature summary matrix to determine an additional value of the molecular property for the new variant protein.

7. The computing system of claim 6, wherein the one or more non-transitory computer-readable storage media store additional computer-executable instructions that, when executed by the one or more processing units, cause the computing system to:

determine respective first values of the plurality of structural features for the modified residues of the plurality of variant proteins using structural models of the plurality of variant proteins.

8. The computing system of claim 7, wherein the parent protein and the plurality of variant proteins include antibodies and determining a value of an individual structural feature of the plurality of structural features for a modified residue of a variant protein of the plurality of variant proteins includes determining a distance between the modified residue and a constant region of the variant protein or determining a distance between the modified residue and a variable region of the variant protein.

9. The computing system of claim 6, wherein:

the one or more non-transitory computer-readable storage media store additional computer-executable instructions that, when executed by the one or more processing units, cause the computing system to generate new variant information that includes an array indicating, for each residue of the new variant protein, whether a respective residue in the new variant protein has been changed with respect to a residue at a corresponding location in the parent protein; and the additional value of the molecular property for the new variant protein is generated based on the new variant information.

10. The computing system of claim 6, wherein the one or more non-transitory computer-readable storage media store additional computer-executable instructions that, when executed by the one or more processing units, cause the computing system to:

determine a value for a structural feature relating to diversity of residues neighboring a variant residue of the variant protein by:

determining a number of hydrophobic residues within a first distance of the variant residue;

determining a number of acidic residues within a second distance of the variant residue;

determining a number of basic residues within a third distance of the variant residue; and determining a number of neutral residues within a fourth distance of the variant residue;

wherein the first distance, the second distance, the third distance, and the fourth distance are based on a tertiary structure of the variant protein.

11. The computing system of claim 6, wherein the one or more non-transitory computer-readable storage media store additional computer-executable instructions that, when executed by the one or more processing units, cause the computing system to:

determine a value for a structural feature of a variant residue of the variant protein by:

determining that the variant residue is located in a positively charged region of the variant protein; or determining that the variant residue is located in a negatively charged region of the variant protein.

12. The computing system of claim 6, wherein:

the one or more non-transitory computer-readable storage media store additional computer-executable instructions that, when executed by the one or more processing units, cause the computing system to:

generate a feature vector by aggregating values for structural features corresponding to each modified residue in the variant protein that is different from an initial residue of the parent protein at respective corresponding positions; and produce the training data by assigning the value of the molecular property for the variant protein to the feature vector.

13. The computing system of claim 6, wherein:

the one or more non-transitory computer-readable storage media store additional computer-executable instructions that, when executed by the one or more processing units, cause the computing system to:

obtain input indicating changes to residues of the parent protein to produce a number of modified residues for a new variant protein; and generate a feature vector by determining individual values for respective structural features for each modified residue of the number of modified residues; and the additional value of the molecular property for the new variant protein is determined based on the feature vector.

14. A method comprising:

performing, by a computing system including one or more processing units and one or more non-transitory computer-readable storage media, a training process for a model to predict values for a molecular property for new variant molecules that correspond to a parent molecule, the training process including:

generating, by the computing system, a structural matrix for a variant molecule, the variant molecule having modified residues that are different from initial residues at corresponding first positions of a parent molecule and the structural matrix indicating respective first values for individual structural features for individual residues of the variant molecule;

modifying, by the computing system, the structural matrix to generate a modified structural matrix for the variant molecule, the modified structural matrix indicating a subset of the first values that corresponds to the modified individual residues;

assigning, by the computing system, a value of a molecular property for the variant molecule to the subset of the first values included in the modified structural matrix; and generating, by the computing system and based on the modified structural matrix and the value for the molecular property, a model to predict values for the molecular property for new variant molecules that correspond to the parent molecule;

generating, by the computing system, a second modified structural matrix that indicates second values for the individual structural features for individual residues of a new variant molecule that are different from individual residues of the parent molecule at corresponding second positions; and applying, by the computing system, the model to the second modified structural matrix to determine an additional value of the molecular property for the new variant molecule.

15. The method of claim 14, comprising:

determining a first value of a first structural feature of a modified residue of the variant molecule by determining an accessibility of the modified residue to a solvent based on proximity of the modified residue to a surface of the variant molecule; and determining a second value of a second structural feature of the modified residue by determining a pKa value of the variant molecule with respect to a pKa value of the parent molecule.

16. The method of claim 14, comprising:

performing one or more statistical operations with respect to the subset of the first values to produce one or more third values for the one or more statistical operations;

generating a structural feature summary matrix that includes the one or more third values in association with the variant molecule and includes a number of additional values for the one or more statistical operations in association with a plurality of additional variant molecules; and determining based on the structural feature summary matrix, a subset of the individual structural features included in the structural matrix.

17. The method of claim 16, wherein the model includes one or more parameters that correspond to the subset of the individual structural features.

18. The method of claim 16, wherein the one or more statistical operations include at least one of determining for the subset of the first values: a sum, a mean, a standard deviation, a skew, a kurtosis, a minimum, a maximum, a product, a sum of log of absolute values, or a mean of log of absolute values.

19. The method of claim 14, wherein the molecular property includes antibody melting temperature, chemical unfolding behavior, solubility, viscosity, aggregation behavior, or percentage of high molecular weight.

20. The method of claim 14, comprising:

obtaining input indicating changes to residues of the parent molecule to produce a number of modified residues for a new variant molecule;

generating a feature vector by determining individual values for respective structural features for each modified residue of the number of modified residues; and wherein the additional value of the molecular property for the new variant molecule is determined based on the feature vector.

* * * * *